US00PP30075P2

(12) United States Plant Patent
Heimovaara

(10) Patent No.: US PP30,075 P2
(45) Date of Patent: Jan. 8, 2019

(54) ***CHRYSANTHEMUM* PLANT NAMED 'ZANMUMAJES RED'**

(50) Latin Name: ***Chrysanthemum* x *morifolium* Ramat.**
Varietal Denomination: Zanmumajes Red

(71) Applicant: Van Zanten Breeding BV, Aalsmeer (NL)

(72) Inventor: Sjoukje Heimovaara, Valkenburg (NL)

(73) Assignee: VAN ZANTEN BREEDING BV, Aalsmeer (NL)

( * ) Notice: Subject to any disclaimer, the term of this patent is extended or adjusted under 35 U.S.C. 154(b) by 0 days.

(21) Appl. No.: 15/732,813

(22) Filed: Jan. 4, 2018

(51) Int. Cl.
*A01H 5/02* (2018.01)

(52) U.S. Cl.
USPC ..... Plt./298
CPC ..... *A01H 5/02* (2013.01)

(58) Field of Classification Search
USPC ..... Plt./298
CPC ..... A01H 5/0255
See application file for complete search history.

*Primary Examiner* — Kent L Bell
(74) *Attorney, Agent, or Firm* — Steptoe & Johnson LLP

(57) ABSTRACT

A *chrysanthemum* plant named 'Zanmumajes' characterized by its small sized blooms with red-purple ray florets and prolific branching; natural season flowering date October 2 (week 40); blooming for a period of five weeks.

3 Drawing Sheets

Botanical designation: *Chrysanthemum* x *morifolium* Ramat.

Cultivar denomination: 'Zanmumajes Red'.

RELATED CULTIVARS

The new plant is a flower color mutant of 'Zanmumajes' (U.S. Plant Pat. No. 26,847)

BACKGROUND OF THE INVENTION

The present invention relates to a new and distinct cultivar of *chrysanthemum* plant, botanically known as *Chrysanthemum* x *morifolium* Ramat., commercially known as a garden mum, and hereinafter referred to by the cultivar denomination 'Zanmumajes Red'. 'Zanmumajes Red' is a product of a breeding and selection program which had the objective of finding flower color mutants from existing parent plants. The new plant comprises a whole plant mutant of the parent *chrysanthemum* named 'Zanmumajes' (U.S. Plant Pat. No. 26,847). A comparison between the parent and 'Zanmumajas Red' is provided in the section description of the invention.

In order to obtain flower color mutants, unrooted cuttings of the parent plant were irradiated in April 2013 at Ziekenhuis, Rotterdam, the Netherlands, with gamma radiation at a dose of 15 Gy. These treated cuttings were then planted in a controlled environment (greenhouse) in Rijsenhout, the Netherlands. In this population of planted cuttings, the new cultivar was discovered as a flower color mutant in October 2013 by Sjoukje Heimovaara in a controlled environment (greenhouse) in Rijsenhout, the Netherlands. The first act of asexual reproduction of 'Zanmumajes Red' was accomplished when after planting of the 'Zanmumajes Red' as a motherplant in December 2013, vegetative cuttings from this 'Zanmumajes Red' were taken and propagated further in Rijsenhout, the Netherlands. In summer, about 6-8 days are needed to initiate roots in cuttings of the new cultivar, after another 5 days rooted plants are formed. The new cultivar has been found to retain its distinctive characteristics through successive propagations.

BRIEF DESCRIPTION OF THE DRAWINGS

The present invention of a new and distinct variety of *chrysanthemum* (of about 19 weeks) is shown in the accompanying drawings, the color being as nearly true as possible with color photographs of this type.

DESCRIPTION OF THE INVENTION

Figure 1:
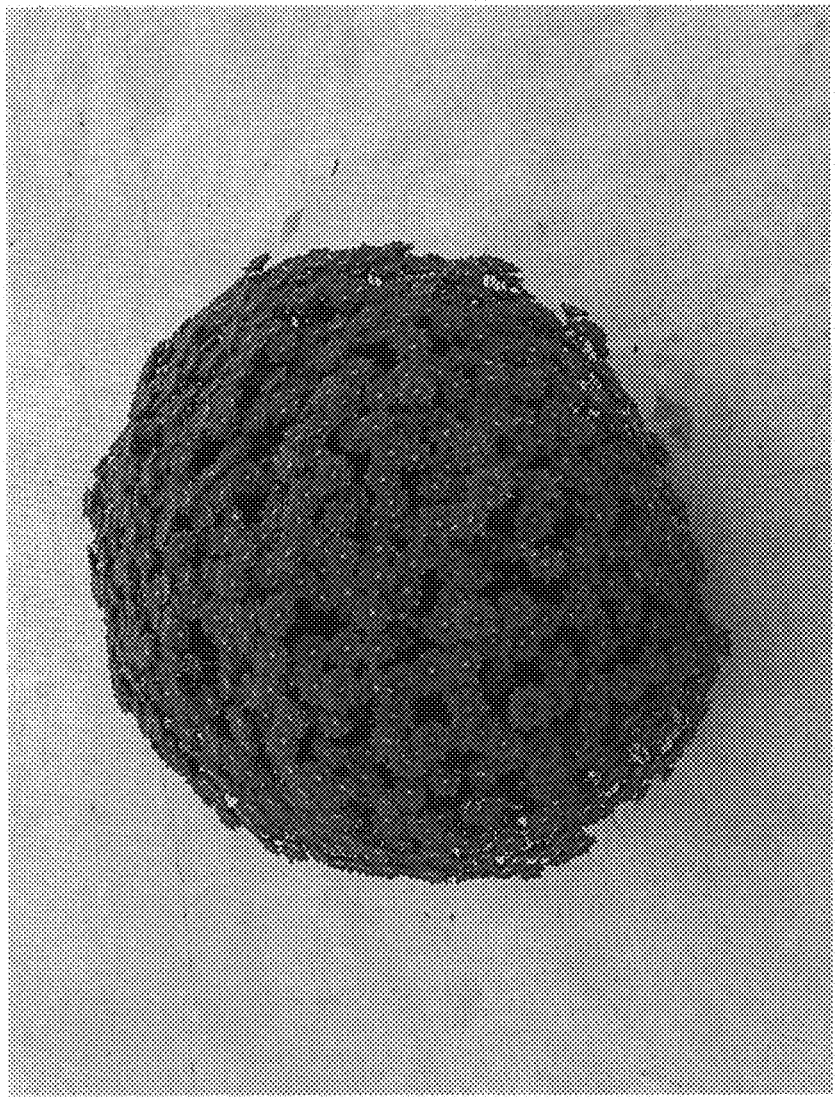
FIG. 1 shows a plant of the cultivar in full bloom.
Figure 2:
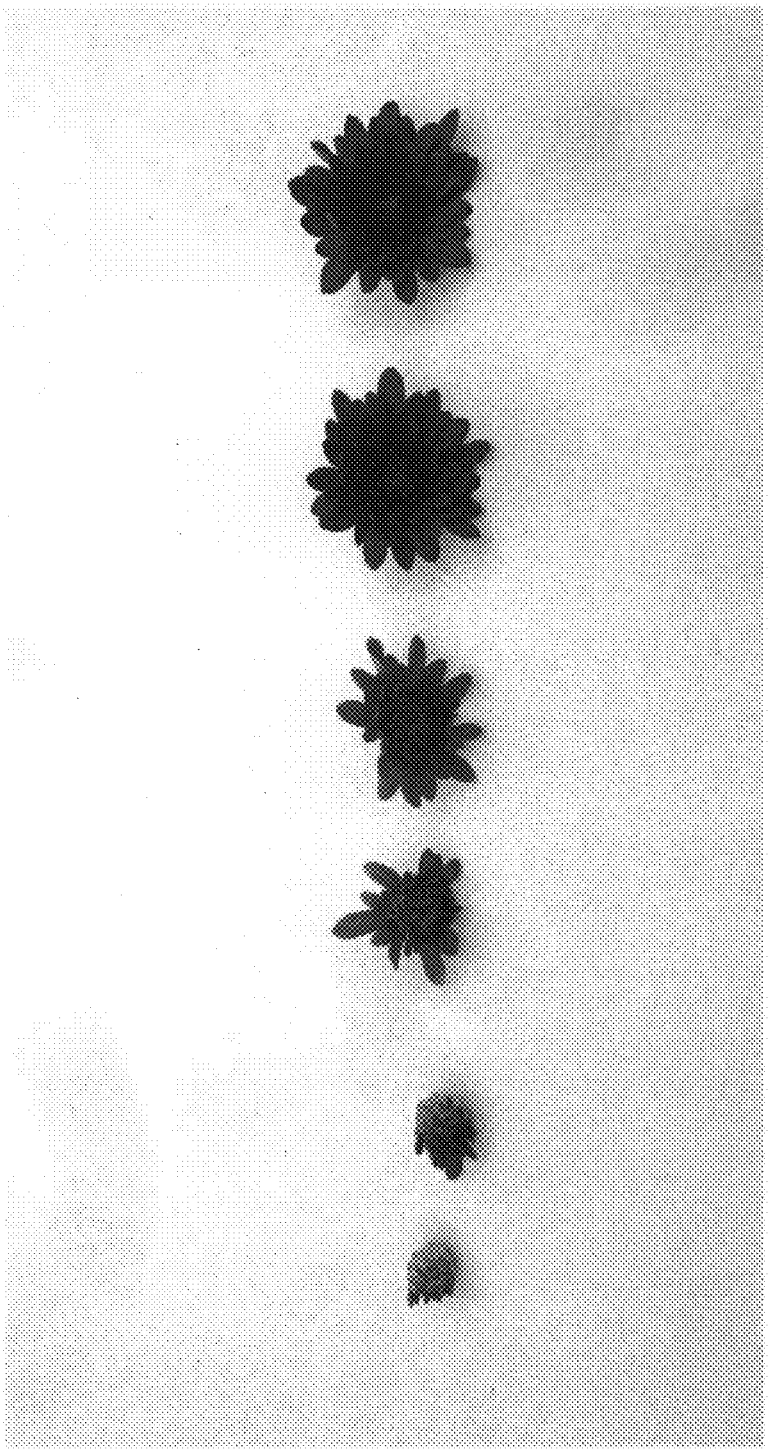
FIG. 2 shows the various stages of blooms of the new cultivar.
Figure 3:
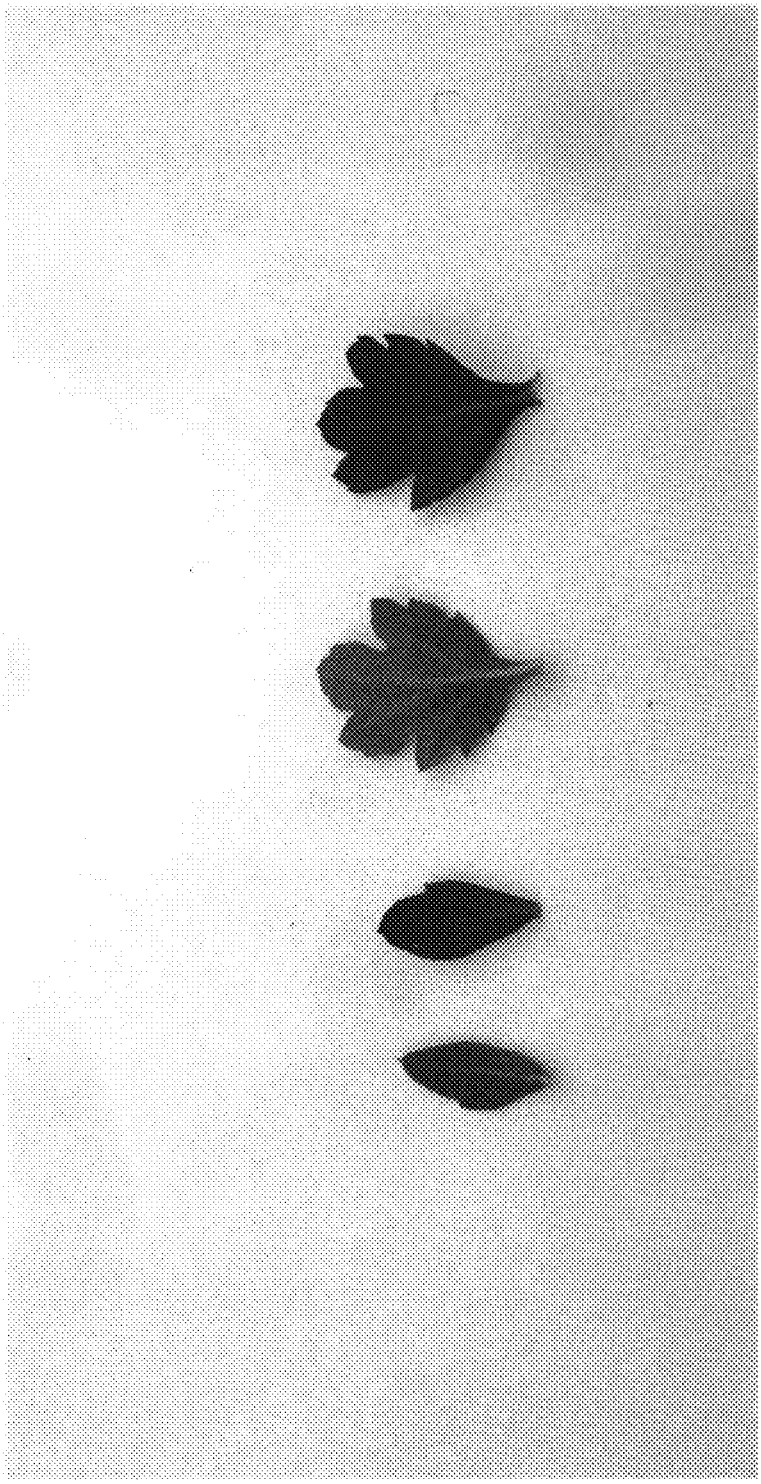
FIG. 3 shows the various stages of foliage of the new cultivar.

The observations and measurements were gathered from plants in the period of 16 to 23 weeks of age grown outdoor in Rijsenhout, the Netherlands, under natural day length and temperature and planted in week 23. The natural blooming date of this crop was October 2 (week 40). The average height of the plants was 35-40 cm. No growth retardants were used. No tests were done on disease or insects resistance or susceptibility. No tests were done on cold or drought resistance. This new variety produces small sized blooms with red-purple ray florets blooming for a period of five weeks.

From the cultivars known to the inventor the most similar existing cultivar in comparison to 'Zanmumajes Red' is 'Zanmumajes'. When 'Zanmumajes' and 'Zanmumajes Red' are being compared the following differences are noticed: (1) Color ray florets. And (2) Presence disc florets. (1) Ray florets of 'Zanmumajes' are purple, while those of 'Zanmumajes Red' are more reddish purple. (2) Disc florets are lacking in 'Zanmumajes' and some disc florets are formed in 'Zamumajes Red', especially when grown indoor.

The following is a description of the plant and characteristics that distinguish 'Zanmumajes Red' as a new and distinct variety.

The color designations are taken from the plant itself. Accordingly, any discrepancies between the color designations and the colors depicted in the photographs are due to photographic tolerances. The color chart used in this description is: The Royal Horticultural Society Colour chart, sixth edition (2015).

TABLE 1

Botanical Description of *Chrysanthemum* × *morifolium* Ramat. 'Zanmumajes Red'

| | |
|---|---|
| **Bud** | |
| Size: | Small; cross-section 4 mm, height 3 mm |
| Shape: | Round |
| Texture: | Pubescent |
| Outside color: | Greyed-green 191A |
| **Phyllaries** | |
| Number: | 21, arranged in 3 rows |
| Shape: | Elliptic |
| Apex: | Acute |
| Base: | Truncate |
| Margin: | Entire |
| Color: | Upper side: Green 137C<br>Lower side: Yellow-green 144C |
| Length and width: | 3 mm; 1.5 mm |
| Texture: | Pubescent |
| **Inflorescences** | |
| Type: | Double |
| Height: | 1 cm |
| Diameter: | 3 cm |
| Peduncle length: | 5.5-6.5 cm |
| Peduncle color: | Green 143C |
| Peduncle diameter: | 1.5 mm |
| Peduncle texture: | Pubescent |
| Peduncle strength: | Weak |
| Number per branch: | About 7-8 inflorescences |
| Duration of flowering: | 5 weeks |
| Seeds: | Produced in small quantities, ovate, Greyed-brown 199A, length 1.5 mm, diameter 0.5 mm; texture: rough with ribs |
| Fragrance: | Faint *chrysanthemum* odor |
| **Color inflorescences** | |
| Center of inflorescence (disc florets): | Immature stage: Green-yellow 1D; Mature stage: Yellow 12A |
| Color of upper side of ray florets: | Greyed-Purple 187B |
| Color of lower side of ray florets: | Greyed-Purple 184B |
| Tonality from distance: | A garden mum with small decorative dark red-purple blooms |
| Color of ray florets after aging of the plant: | Greyed-Purple 183D |
| **Ray florets** | |
| Number of types | One |
| Type: | Ligulate |
| Rows: | 10-12 |
| Texture: | Upper and lower side smooth |
| Number: | 100-110 |
| Shape: | Elliptic |
| Apex: | Pointed |
| Base: | Attenuate |
| Cross-section: | Flat |
| Longitudinal axis: | Straight |
| Length of corolla tube: | 2 mm |
| Diameter corolla tube: | 0.8-1 mm |
| Ray floret margin: | Entire |
| Ray floret length: | 1-1.5 cm |
| Ray floret width: | 2-4 mm |
| Ratio length/width: | Medium |

TABLE 1-continued

Botanical Description of *Chrysanthemum* × *morifolium* Ramat. 'Zanmumajes Red'

| | |
|---|---|
| **Disc florets** | |
| Disc diameter: | 1-2 mm |
| Distribution of disc florets: | Small number in center of inflorescences |
| Shape: | Tubular |
| Color: | Yellow-green 145C at base to Green-yellow 1D at apex |
| Length: | 2 mm |
| Diameter: | 1 mm |
| **Receptacle** | |
| Color: | Yellow-green 145D |
| Shape: | Domed raised |
| Height: | 3 mm |
| Diameter: | 2.5 mm |
| **Reproductive Organs** | |
| Androecium: | Present in only disc florets |
| Stamen length: | 2 mm |
| Stamen color: | Yellow-green 144A |
| Anther color: | Yellow 2A |
| Pollen: | Low amount |
| Pollen color: | Yellow 12A |
| Gynoecium: | Present in ray and disc florets |
| Style color: | Yellow-green 154C |
| Style length: | 3 mm |
| Stigma color: | Yellow 7A |
| Stigma width: | 1 mm |
| Ovary: | Enclosed in calyx; color: Yellow-green 149D |
| **Plant** | |
| Type: | Bushy |
| Growth habit: | Spherical shape |
| Growth rate: | Medium |
| Height: | 35-40 cm |
| Width: | 50 cm |
| Stem color: | Greyed-brown 199A |
| Stem strength: | Weak |
| Stem brittleness: | Brittle |
| Stem anthocyanin coloration: | absent |
| Internode length: | 2 cm |
| Length of lateral branch: | From top to bottom 20 cm |
| Lateral branch color: | Green 138B |
| Lateral branch, attachment: | Weak |
| Lateral branch diameter: | 2 mm |
| Lateral branch texture: | Pubescent with ribs |
| Branching (average number of lateral branches): | Dense with 9 breaks after pinching |
| Natural season blooming date: | October 2 (week 40) in Rijsenhout, The Netherlands. |
| Roots - habits: | Fine, freely branching |
| Roots - color: | White 155D |
| **Foliage** | |
| Glossiness: | Leaf upper side: very weak<br>Leaf lower side: very weak |
| Leaf color: | Upper side: Green 138A<br>GLower side:reen 139C |
| Color midvein: | Upper side: Yellow-green 147D<br>Lower side: Yellow-green 148D |
| Size: | Small; length 3-4.5 cm, width 1.2-2.4 cm |
| Quantity (number per lateral branches): | 20-22 |
| Shape: | Elliptic to widely elliptic |
| Texture upper side: | Sparsely pubescent |
| Texture under side: | Pubescent |
| Venation arrangement: | Palmate |
| Shape of margin: | Serrated |
| Shape of base of sinus between lateral lobes: | Rounded |
| Margin of sinus between lateral lobes: | Diverging |

TABLE 1-continued

| Botanical Description of *Chrysanthemum* × *morifolium* Ramat. 'Zanmumajes Red' | |
|---|---|
| Shape of base: | Attenuate |
| Apex: | Mucronulate |
| Petiole attitude: | Moderately upwards |
| Petiole length: | 0.2-0.5 cm |
| Petiole diameter: | 1.5 mm |
| Petiole color: | Yellow-green 147D |
| Stipules: | Very small, about 8 mm, at leaves at lower part of the branches |

TABLE 2

| Differences with the comparison variety, when grown under identical conditions | | |
|---|---|---|
| | 'Zanmumajes Red' | 'Zanmumajes' |
| Ray floret upperside color | Greyed-purple 187B | Purple N77B |
| Presence disc florets | Few | Lacking |

I claim:

1. A new and distinct *chrysanthemum* plant named 'Zanmumajes Red' as described and illustrated.

* * * * *